(12) United States Patent
Su

(10) Patent No.: US 6,404,210 B1
(45) Date of Patent: Jun. 11, 2002

(54) DIMENSIONALLY STABLE SENSOR FOR MONITORING TERMITE ACTIVITY

(75) Inventor: Nan-Yao Su, Plantation, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 09/260,961

(22) Filed: Mar. 2, 1999

(51) Int. Cl.[7] .............................................. G01R 27/08
(52) U.S. Cl. .................................................... 324/692
(58) Field of Search ........................ 324/692; 424/405, 424/409, 410, 84; 43/131

(56) References Cited

U.S. PATENT DOCUMENTS

| | | |
|---|---|---|
| 3,564,750 A | 2/1971 | Burgess |
| 3,743,581 A | 7/1973 | Cady et al. |
| 3,943,750 A | 3/1976 | McLaughlin |
| 3,949,353 A | 4/1976 | Waters et al. |
| 4,043,073 A * | 8/1977 | Basile .......................... 43/124 |
| 4,075,607 A | 2/1978 | Abe |
| 4,141,006 A | 2/1979 | Braxton |
| 4,153,881 A | 5/1979 | Permut et al. |
| 4,260,981 A | 4/1981 | Yamauchi et al. |
| 4,567,367 A | 1/1986 | Brown de Colstoum et al. |
| 4,812,741 A | 3/1989 | Stowell |
| 4,893,248 A | 1/1990 | Pitts et al. |
| 4,937,555 A | 6/1990 | Litzkow et al. |
| 4,941,356 A | 7/1990 | Pallaske |
| 4,996,655 A | 2/1991 | Chadwick et al. |
| 5,121,344 A | 6/1992 | Laage et al. |
| 5,126,679 A | 6/1992 | Spry |
| 5,132,968 A | 7/1992 | Cephus |
| 5,285,688 A | 2/1994 | Robbins et al. |
| 5,329,726 A | 7/1994 | Thorne et al. |
| 5,381,136 A | 1/1995 | Powers et al. |
| 5,475,742 A | 12/1995 | Gilbert |
| 5,485,142 A | 1/1996 | Stute et al. |
| 5,555,672 A | 9/1996 | Thorne et al. |
| 5,564,222 A | 10/1996 | Brody |
| 5,571,967 A * | 11/1996 | Tanaka et al. ................. 73/587 |
| 5,575,105 A | 11/1996 | Otomo |
| 5,592,774 A | 1/1997 | Galyon |
| 5,815,090 A * | 9/1998 | Su .............................. 340/870 |
| 5,983,558 A * | 11/1999 | Las et al. ..................... 43/131 |

FOREIGN PATENT DOCUMENTS

| | | |
|---|---|---|
| EP | 0283142 | 9/1988 |
| JP | 7-142827 | 6/1995 |
| JP | 9-98701 | 4/1997 |
| JP | 9-121742 | 5/1997 |
| JP | 10-56935 | 3/1998 |
| JP | 10-84834 | 4/1998 |
| WO | WO 93/23998 | * 12/1993 |

OTHER PUBLICATIONS

Scheffrahn et al., (1997) *Journal of Economic Entomology*, vol. 90, No. 2, pp. 492–502.
Nan-Yao Su, (1994) *Journal of Economic Entomology*, vol. 87, No. 2, pp.389–397.

* cited by examiner

Primary Examiner—Safet Metjahic
Assistant Examiner—Etienne P LeRoux
(74) Attorney, Agent, or Firm—McDonnell Boehnen Hulbert & Berghoff

(57) ABSTRACT

The present invention pertains to a dimensionally stable sensor that minimizes false positive responses caused by high humidity, rainfall, or temperature fluctuation while maintaining true positive responses attained from termite activity. The invention further pertains to a method for continually monitoring termite activity by utilizing dimensionally stable sensor(s).

13 Claims, 7 Drawing Sheets

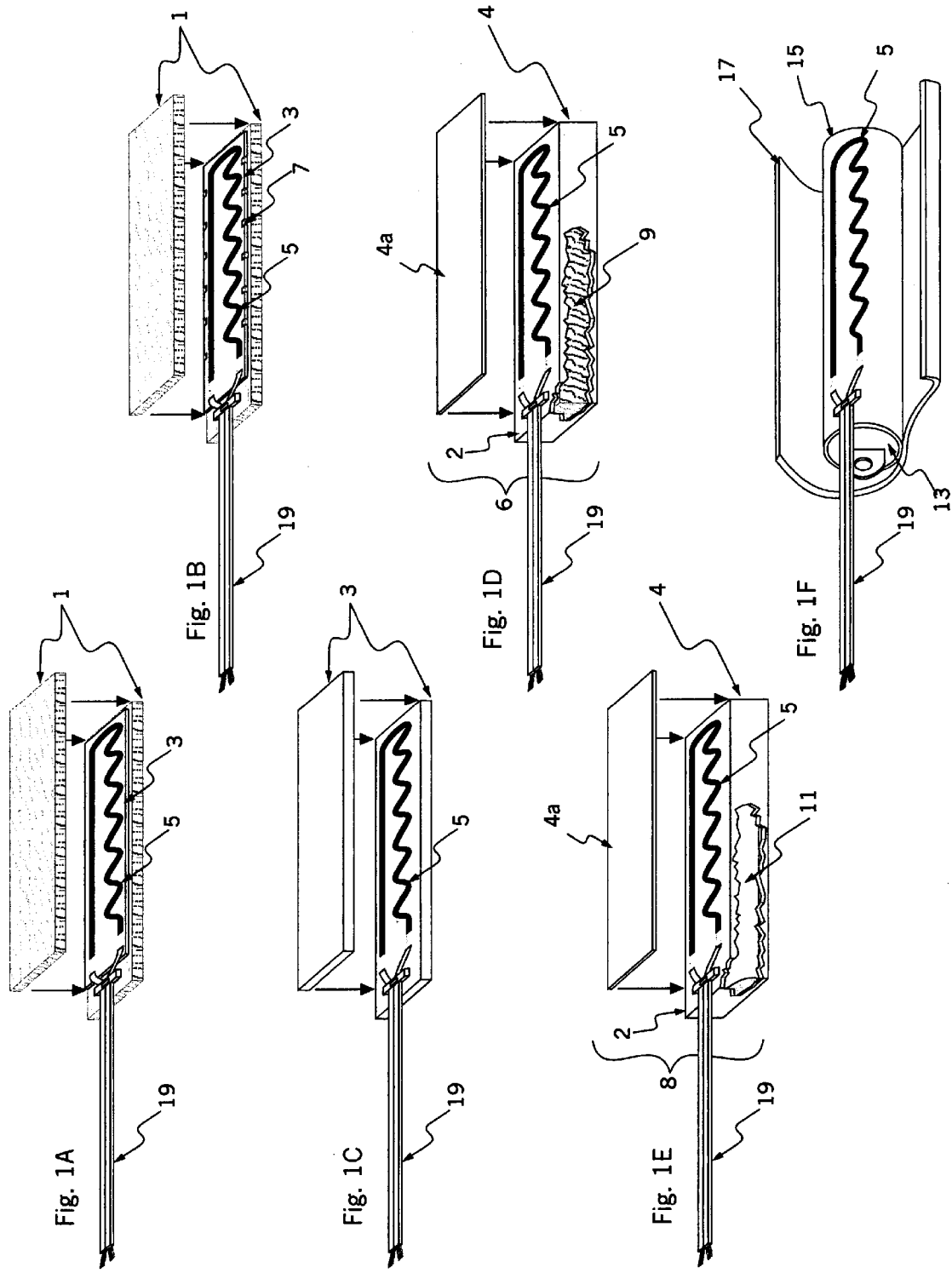

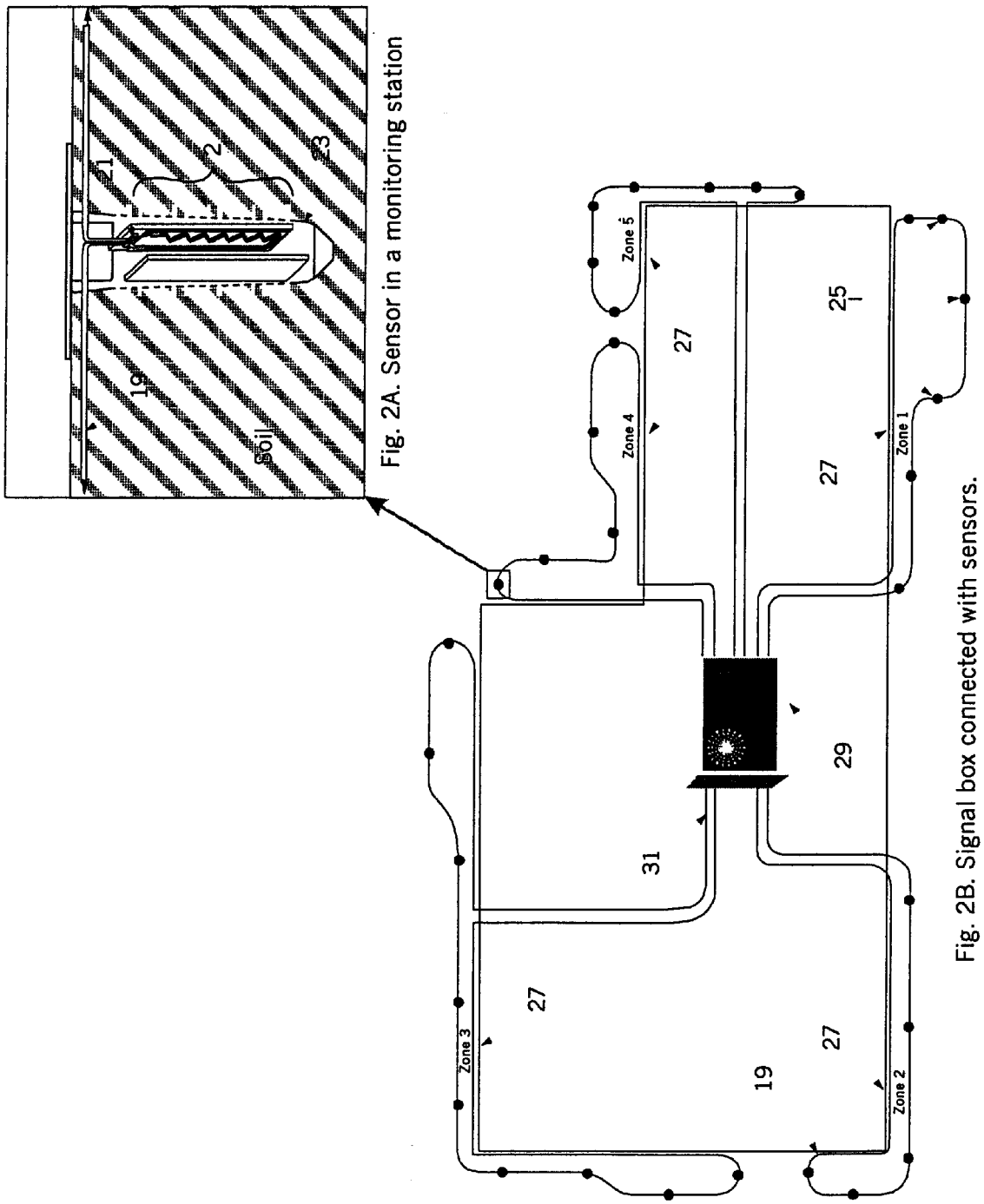
Fig. 2A. Sensor in a monitoring station
Fig. 2B. Signal box connected with sensors.

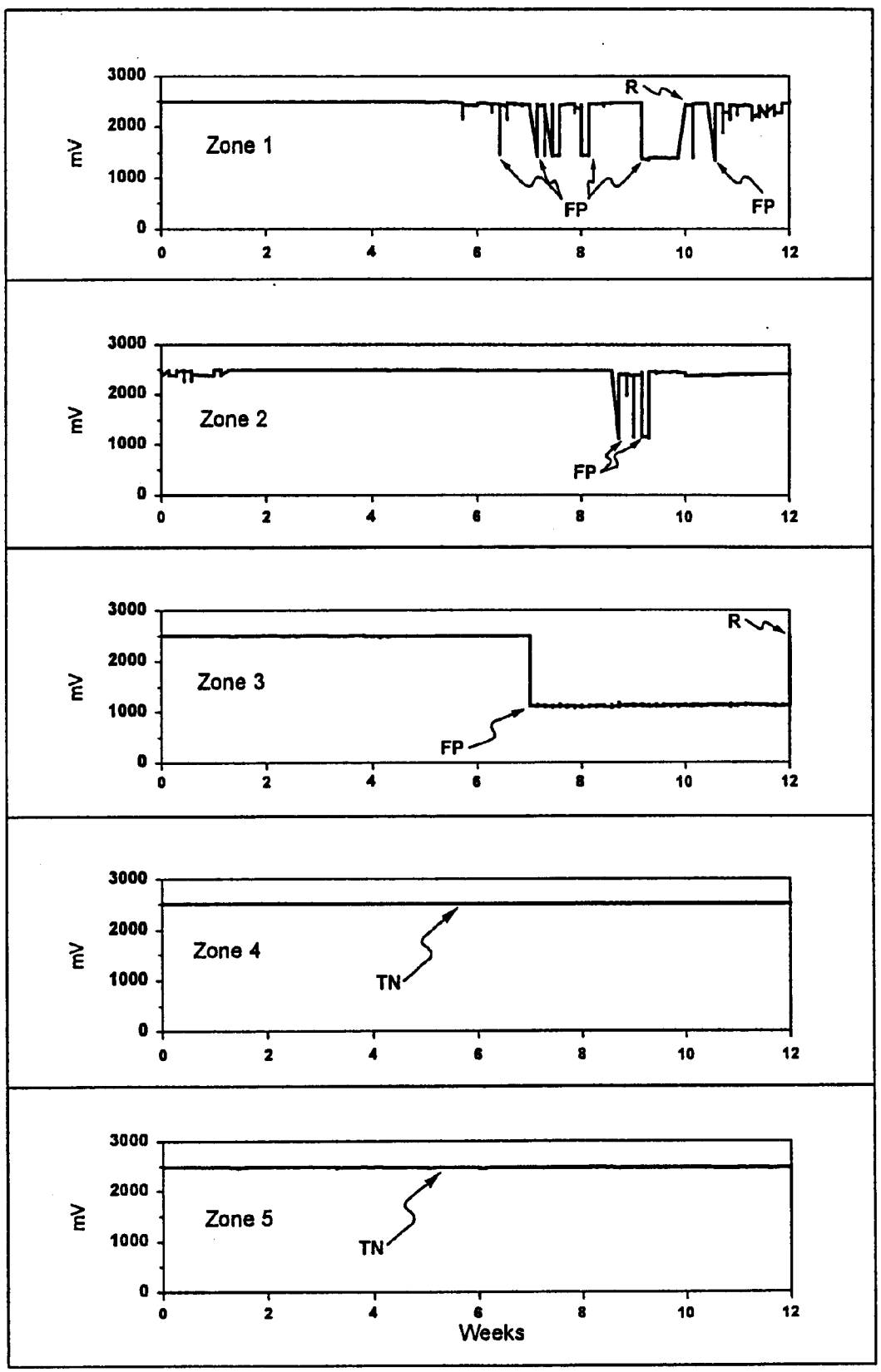
Fig. 3A. Wood sensors in non-infested site (Site I)

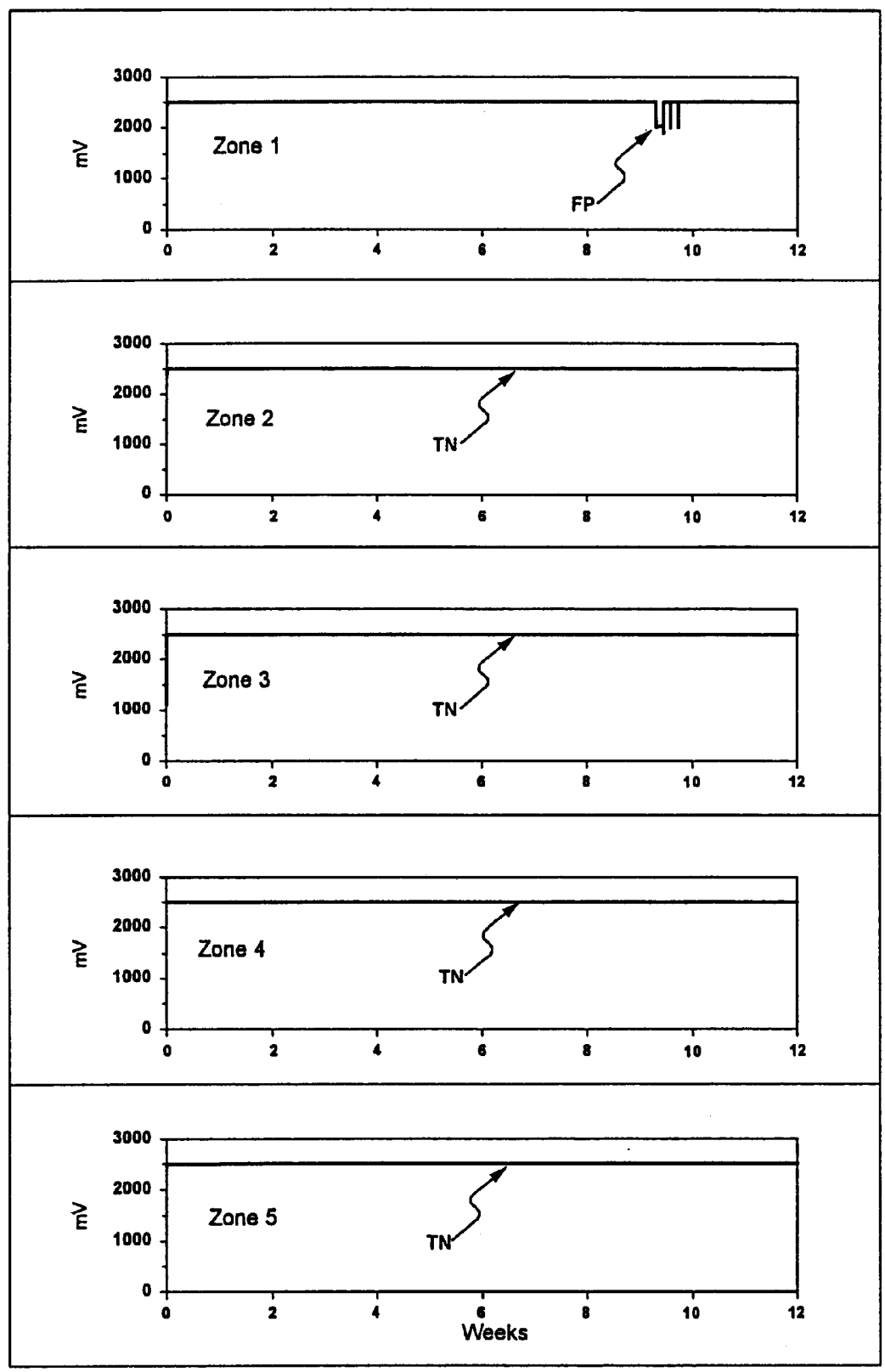
Fig. 3B. DS sensors in non-infested site (Site I)

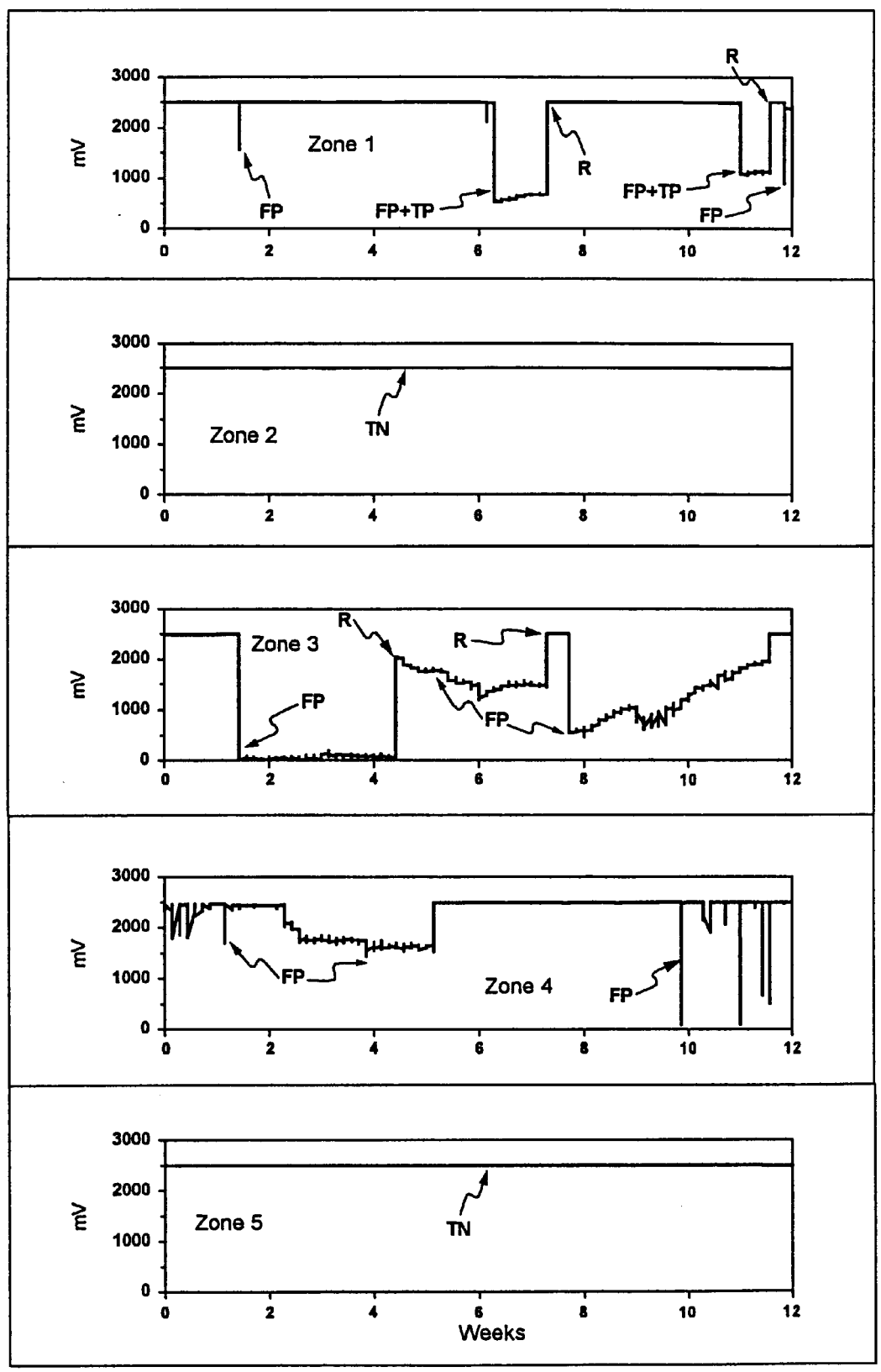
Fig. 4A. Wood sensors in infested site (Site II)

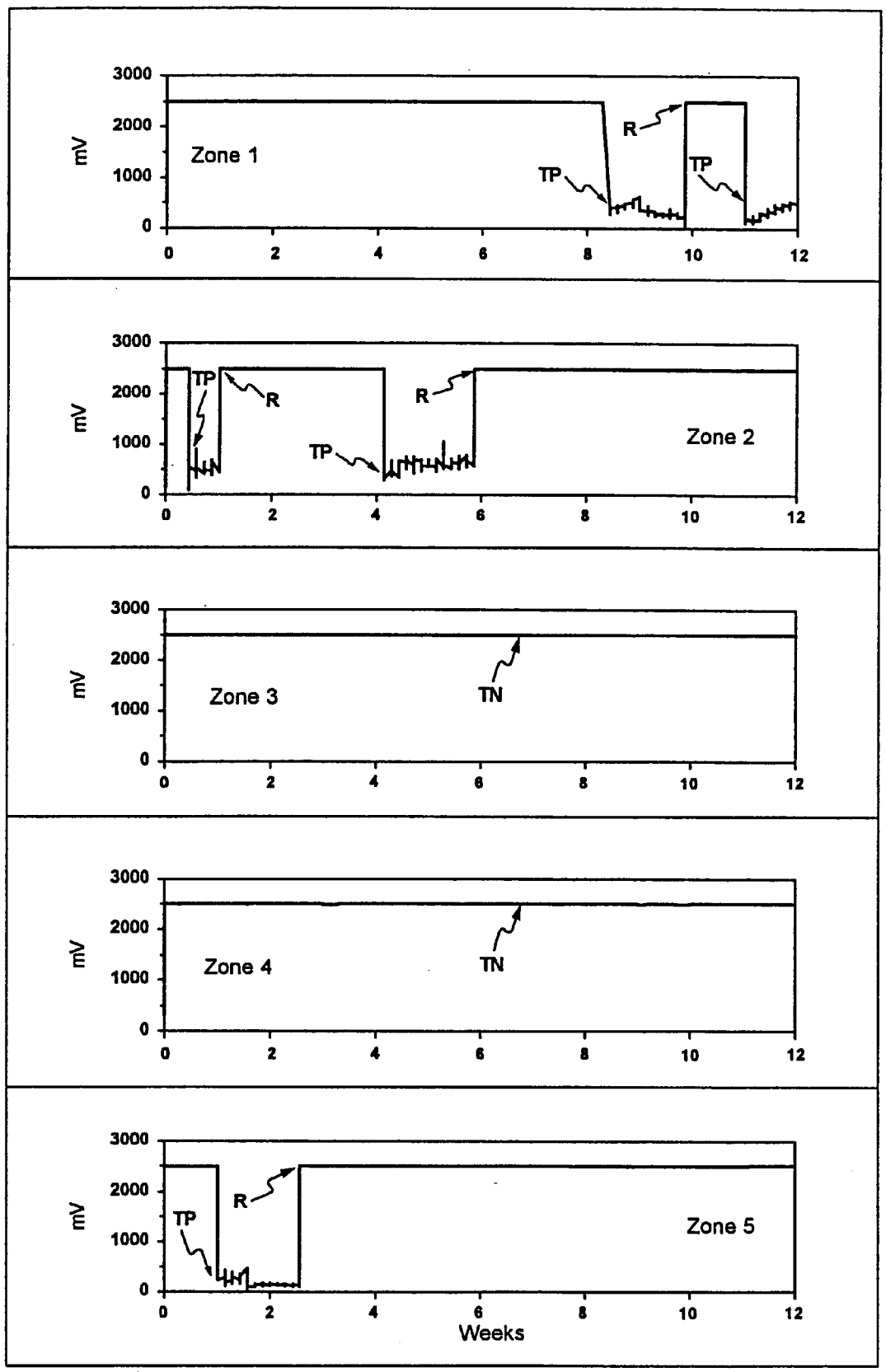
Fig. 4B. DS sensors in infested site (Site II)

DIMENSIONALLY STABLE SENSOR FOR MONITORING TERMITE ACTIVITY

BACKGROUND OF THE INVENTION

1. Field of the Invention

This invention relates to sensors for detecting termite activity. This invention further relates to a method of detecting termite activity.

2. Description of the Related Art

Over the last four decades, control of subterranean termites has heavily relied on the use of liquid insecticides. Typically 100–200 gallons (or 5–10 kg active ingredient) of insecticide are applied to soil surrounding or beneath a house to exclude soil borne termites from structures. Because a subterranean termite colony can contain several hundred thousand to millions of termites that forage up to 300 feet from the nest, the majority of termites in a colony usually survive such soil treatments. In recent years, with less persistent insecticides being used as chemical barriers, re-infestation of surviving termites has become more frequent.

One alternative to conventional soil treatment is the use of slow-acting bait to control populations of subterranean termites. The monitoring/baiting program incorporating an insect growth regulator, hexaflumuron, as described by Su, N.-Y., *Field Evaluation of a Hexaflumuron Bait for Population Suppression of Subterranean Termites (Isoptera: Rhinotermitidae)*, Journal of Economic Entomology 87: 389–397 (1994), is now commercially marketed as the Sentricon® Termite Colony Elimination System. To date there are numerous research data that demonstrate the elimination of colonies of various species of subterranean termites by the Sentricon system in the United States, Japan, Australia and Europe. Unlike conventional soil insecticide treatment, the monitoring/baiting program relies on routine monitoring to protect a given area. When termites are found in the monitoring stations, the monitoring devices are replaced with baits containing hexaflumuron. Baits containing the active ingredient are not used until termites are detected. This arrangement drastically reduces pesticide use for control of subterranean termites. It usually takes less than 1 gram of hexaflumuron to eliminate a colony of subterranean termites. Due to its low environmental impact, hexaflumuron is the first compound to be registered under the EPA's Reduced Risk Pesticide Initiative.

One of the key components of the Sentricon system is the monitoring step. U.S. Pat. No. 5,329,726 (Thorne et al., Jul. 19, 1994) also adopted a "diagnostic" phase before bait placement. However, this manual on-site monitoring is also the most labor intensive and costly element of the system.

There are other techniques available to detect the presence of termites in wood or soil. For example, Japanese Pat. No. 9-121742 (Sharp K.K., 5/1997) discloses an apparatus in which an optical sensor is employed to detect termite movement in a pre-drilled foraging tunnel in a wood block. However, the presence of subterranean termites is usually associated with elevated moisture (Su & Scheffrahn 1991, IRG/WP/1504). U.S. Pat. Nos. 4,812,741 (Stowell et al., Mar. 14, 1989) and 5,126,679 (Spry, Jun. 30, 1992) teach the use of a moisture sensor to signal the presence of termites. Further, termites are known to produce gases such as $CO_2$ and methane. Such gases can be detected in the ground by use of subterranean probes (U.S. Pat. No. 3,943,750; McLaughlin et al., Mar. 16, 1976). Unfortunately, many other factors can produce moisture or subterranean gases, such as leaky plumbing, rainfall, putrefaction or fungal decay. Because these conditions are not unique to termite activity, monitoring stations adapted with these sensors or probes can cause false alarms and account for frequent, costly, and unnecessary on-site inspections.

Methods and devices for detecting infestation of termites have recently emerged. For instance, U.S. Pat. No. 5,592,774 (Galyon, Jan. 14, 1997) discloses a two-sensor system in which both sensors detect termite-presence conditions such as high humidity and gases. It is expected that when termites invade only one sensor, its condition (high moisture, gases, etc.) would be significantly different from the other, thus signaling the presence of termites. There is no guarantee, however, that only one sensor is invaded by termites, especially in areas of high termite population. Therefore, this arrangement does not address the problem of both sensors being simultaneously invaded by termites, thereby signaling a false negative response. In addition, microenvironment differences (slight humidity difference due to water flow in soil, etc.) can signal a false positive response with this type of system. Moreover, the presence of other soil dwelling insects such as earthworms, ants, and beetle larvae also produce termite-presence conditions such as high humidity and gases. Again, because such conditions are not unique to termite activity, invasion by these soil dwelling insects will cause false positives and costly, unnecessary on-site inspections.

Another method of termite monitoring focuses on detecting termite feeding by vibrations or sound transmitted through wood when termites tear and break wood fibers (U.S. Pat. No. 4,941,356, Pallaske 7/1990; Japanese Pat. H-7142827, Ikari 6/1995; PCT Publication No. WO93/23998). Such acoustic signals, however, can also be generated by other wood destroying insects such as powder beetles, bark beetles, house boarder, and carpenter ants, which also break wood fibers and thus can cause false positive responses. Moreover, these methods and apparatuses typically employ elaborate sensors that detect a narrow range of sound or vibration frequency, costly amplifiers to enhance the signals, and complex computer chips to interpret the signals.

These acoustic emission devices can be useful as handheld tools to detect activities of termites and other wood destroying insects in structures (Scheffrahn et al. 1997, *J. Econ. Entomol.* 90: 492–502). Because 30–40 monitoring stations are needed to protect a house for a monitoring/baiting program, however, it is cost-inhibitory to utilize such acoustic emission devices (generally >$1,000 per unit) in all of the stations. It is therefore highly desirable to incorporate a facile, inexpensive and specific termite-detecting sensor within the modern monitoring/baiting programs.

For example, PCT Publication No. WO 93/23998 (Dec. 9, 1993) discloses a simple efficient sensor that utilizes a thin strip of conductive soft metal (i.e. aluminum foil) placed over wooden blocks or stakes. It is proposed in this application that termites feeding on the wooden blocks break the soft metal circuit that is detectable by the lack of electric conductivity. Japanese Pat. No. 9-98701 (Ikari Shodoku K.K., Apr. 15, 1997) describes a termite-detecting device comprising an electrically conductive circuit secured on a medium damageable by termite feeding, such as paper.

A problem with using material such as wood, paper or other materials containing exclusively cellulose as the feeding medium, however, is that both false positive and false negative responses are common when sensors utilizing these materials are placed in the soil for an extended period of time. Outdoor elements such as rainfall, temperature fluctuation, and high humidity and biotic factors such as fungal decay and activity from other insects can trigger false positive responses. In fact, sensors incorporating wood or paper material produce false positive responses when conductive circuits are broken by expansion of cellulose-containing materials due to high humidity, rainfall or temperature fluctuation. Fungal decay and other insect activity such as tunneling by beetles or carpenter ants in wood also cause the circuit to break. Moreover, wet wood or paper can allow conductivity even when the circuit is broken by termites, thus causing a false negative response. It is for these reasons that sensors or termite-detecting devices that incorporate wood or paper, while arguably effective for a short term under field conditions, may not be ideally employed in a continuing monitoring program.

Therefore, a sensor used in a long-term continuous monitoring program for subterranean termites should desirably be specific to termite activity (true positive response). Furthermore, it should desirably not be susceptible to false positive responses caused by other environmental or biotic factors, i.e. the circuit should remain intact for an extended period (for example, months or years) absent the presence of termite activity.

Other detection apparatuses such as those taught in U.S. Pat. No. 3,564,750 (Burgess, Feb. 23, 1971), WO 93/23998 (Dec. 9, 1993) and Japanese Pat. No. 9-98701 (Ikari Shodoku K.K., Apr. 15, 1997) typically address the need for the true positive response, i.e. to be able to detect termite feeding, but do not address the issue of false negative responses.

SUMMARY OF THE INVENTION

This invention relates to a dimensionally stable (DS) sensor for use in a continuing monitoring program to detect termite activity.

Specifically, the present invention discloses a sensor that is specific to termite activity and not to the activity of other soil dwelling or wood destroying insects. The sensor is also dimensionally stable enough to be unaffected by environmental factors such as rainfall, high humidity, and temperature fluctuation, and by biotic factors such as fungal decay, which is typically associated with wood and other cellulose-containing materials.

The DS sensor comprises a dimensionally stable monitoring substrate. The monitoring substrate comprises a polymeric termite edible material that is resistant to dimensional expansion or contraction caused by meteorological elements such as changes in ambient humidity and/or temperature. Further, an electrically conductive circuit material is affixed to or embedded in one side of the monitoring substrate. The electrically conductive circuit material is breakable by termite activity, such as termite feeding or termite tunneling, and forms a continuous electrical bridging circuit such that when termite feeding breaks the electrically conductive circuit material, the continuous electrical bridging circuit is broken. The continuous electrical bridging circuit is also resistant to breakage for an extended period of time from exposure to meteorological elements such as changes in ambient humidity and/or temperature fluctuation. Thus, the dimensionally stable sensor is less susceptible to false positive responses and/or false negative responses in monitoring termite activity.

Alternatively, the sensor comprises a casing that houses the termite edible monitoring substrate. The casing itself is termite edible and serves to substantially isolate the substrate from the environment such that the monitoring substrate is effectively rendered dimensionally stable. The electrically conductive circuit material, in turn, is affixed to or embedded in the monitoring substrate.

The present invention also incorporates a tactile stimuli (TS) in the sensor to induce termite tunneling at desired locations and or directions, since termites tend to initiate tunneling or feeding in substrates at any point of departure from smooth continuous surfaces that allow termite mandibles to grasp. By placing these TS at certain positions of a sensor in relation to the conductive circuits, timing of circuit breakage by termites can be regulated.

The present invention also teaches a method for continually monitoring termite activity in a particular site by utilizing at least one DS sensor and a detector for detecting breakage of the circuit due to termite feeding. The method provides for a more reliable way to specifically detect termite activity from other environmental and biotic factors, thus making it less susceptibe to false positive and false negative responses than other termite-detecting systems.

BRIEF DESCRIPTION OF THE DRAWINGS

FIG. 1A shows a DS sensor with a silver particle circuit placed on a closed-cell polyethylene sheet that in turn is sandwiched between two wood pieces.

FIG. 1B shows the sensor of FIG. 1A with small tactile stimulating notches made at the edge of the closed-cell polyethylene sheet.

FIG. 1C shows a DS sensor with a silver particle circuit placed on a closed-cell polyethylene sheet and covered with another polymer sheet.

FIG. 1D shows a DS sensor with a silver particle circuit placed on a polymer block or wrapping containing a termite-monitoring device and covered with another polymer sheet.

FIG. 1E shows the DS sensor of FIG. 1D, the polymer block or wrapping containing termite bait instead of a termite-monitoring device.

FIG. 1F shows the DS sensor of FIG. 1E, the termite bait contained within a plastic tube wrapping inside the polymer block or wrapping.

FIG. 2A shows a DS sensor in a plastic monitoring station.

FIG. 2B shows a DS sensors grouped in several zones that are cable-connected to a signal box.

FIG. 3 compares voltage readings (mV) of wooden sensors with those of DS sensors, one of each being placed in a series of 5 separate zones without termite populations. "FP" represents false positive, "TN" represents true negative and "R" represents replaced sensor.

FIG. 4 compares voltage readings (mV) of wooden sensors with those of DS sensors, one of each being placed in a series of 5 separate zones with termite populations. "TP" represents true positive.

DETAILED DESCRIPTION OF THE PREFERRED EMBODIMENT

Figure 5:
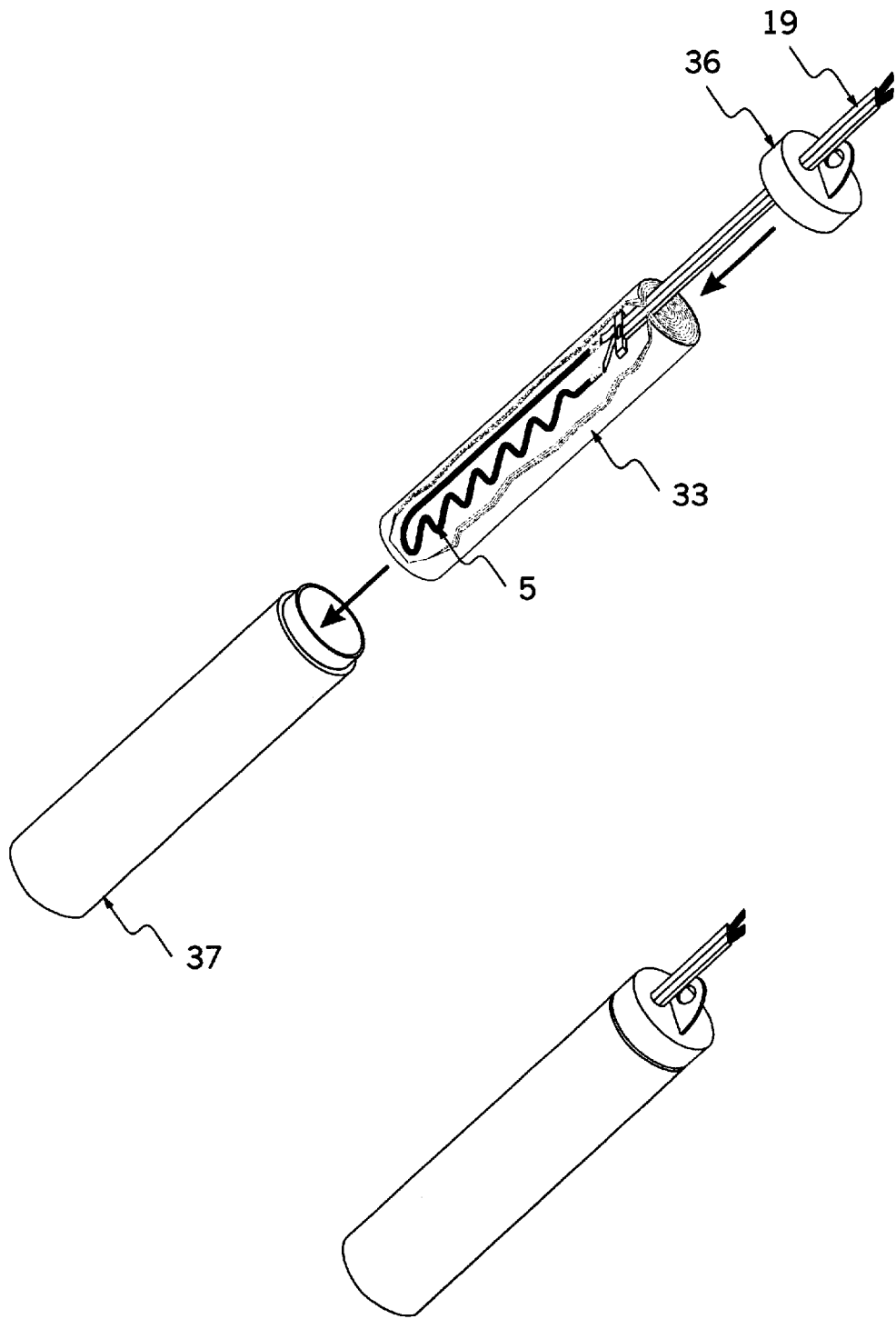
FIG. 5 shows a DS sensor encased in an environmentally isolating material in which the circuit is placed on cellulose-based material such as paper, wood or particle board.

The preferred embodiment of the subject invention pertains to a sensor for detecting termite activity comprising a substrate on which an electrically conductive circuit is attached. Both substrate and electric circuit are soft enough to be broken by termite activity such as feeding, tunneling or excavation. Preferably the circuit can be readily adhered to the substrate. However, the sensor is dimensionally stable and durable against environmental factors such as rainfall, high humidity, and temperature fluctuation, and biotic factors such as fungal decay. Further, the circuit is not readily broken by the activity of other soil or wood dwelling organisms such as earthworms, ants, beetle larvae, carpenter ants, powderpost beetles, bark beetles, or wood boarders.

The electrically conductive circuit is preferably made from such materials as silver particle traces, aluminum foil, conductive polymers such as conductive epoxy glue, or any particles of conductive materials bonded together with glue, including polymers, gold, copper, nickel or iron (see, for example, WO 98/18319). Examples of materials suitable for use as the substrate are closed-cell polyethylene, expanded polystyrene (Styrofoam®), expanded polypropylene, textured polyethylene (ArtFoam®), expanded polyurethane, vinyl, closed cell vinyl foam, polyol resin of pollymeric diisocyanate (InstaFoam®), absorbent paper with polyethylene backing, cellular rubber, and sponge rubber. In fact, many types of polymer-based padding sheets or foam blocks (with or without cellulose) that are used as packaging materials, insulation, or laboratory bench top protection sheets can be used for this purpose. These materials possess the characteristics of dimensional stability against rainfall, high humidity, temperature fluctuation, and fungal decay; yet, their soft and foam texture are uniquely preferred by termites for feeding, tunneling and excavation. Field experiments consistently show that other soil dwelling organisms or wood destroying insects do not tunnel or excavate through these materials. Thus, these dimensionally stable materials are specific to termite activity.

Several embodiments of the present invention are depicted in FIG. 1. FIG. 1A, for example, shows a silver particle circuit 5 placed on the surface of a closed-cell polyethylene sheet 3 and sandwiched between two wooden pieces 1 so that the circuit is protected from breakage during handling or shipping. Covering the circuits with a piece of wood or polymer creates small crevices, i.e. tactile stimuli (TS), that are preferred by termites for excavating and tunneling. Thus, termites readily break the circuits in the crevices. Additionally, small notches 7 are desirably made at the edge of the polymer foam 3 (FIG. 1B) so that when the foam 3 is sandwiched by two wood pieces 1, the notches 7 serve as TS that induce termite tunneling. Termites entering the notches 7, or TS, are directed towards the conductive circuits 5 to ensure circuit breakage. The small notches 7 can be added to the polymer sheet for all embodiments of the invention to facilitate termite entry.

One advantage of using the wooden piece sandwich 1 is that termite feeding in wood often extends to the polymer-based DS sensor to break the circuit. But the polymer-based DS sensors also can be used without wooden pieces as shown in FIG. 1C. The crevices produced by two pieces of polymer sheets can also function as TS. Field experiments show that termites readily tunnel into the polymer foam materials and break the attached circuits. Because wood often decays in highly humid environment within several months, the non-wood sensor can remain in soil for longer period of times without being replaced.

A more preferred embodiment of the invention combines the DS sensor 2 with a termite-monitoring device 9 (FIG. 1D) or with bait 11 (FIG. 1E). The monitoring device 9 or bait 11 can be enclosed in a polymer block 4 on which the circuit 5 is placed or embedded to form a sensor/monitor 6 or sensor/bait 8 unit. Another sheet of polymer 4a is then placed over the drawn circuit 5 for protection and to form an interface for termite tunneling. Because the wood or cellulose material employed in this embodiment of the invention is protected by the DS material, the longevity of such a monitoring device is extended.

One advantage of the DS sensor/bait unit 8 is that immediate action is not required when the sensor detects termites, because the termites usually take a few weeks to totally consume the bait. Another embodiment of the invention is to enclose a bait-containing plastic tube 13 (such as the Baitube® used in Sentricon system) within a circuit-containing layer of polymer 15 that itself is covered with another layer of polymer 17 (FIG. 1F).

Another embodiment is shown in FIG. 2A, in which electric cables 19 are attached over the circuit ends 21 of the DS sensor 2, which is housed in a monitoring station 23. The station 23 can be monitored individually by measuring the electric conductivity or can be connected with other stations 25 to form a continuous zone(s) 27 of sensors (FIG. 2B). FIG. 2B also depicts a more preferred embodiment, which is to connect several continuous zones 27 to a signal box 29 using cables 31 or alternatively, through wireless means. The signal box 29 is designed to alert the homeowner or pest control operator of the circuit breakage by visual or audible signals. Alternatively, the sensors can be connected to a data collection unit (datalogger) for continuous monitoring of the circuit. The data can be downloaded to a central computer using a modem and a telephone line as described in WO 98/18319, the entirety of which is incorporated herein by reference.

Another preferred embodiment of the invention is depicted in FIG. 5. The figure shows a silver particle circuit 5 placed on the surface of a termite edible-based sheet 33. The termite edible-based sheet is entirely enclosed by a casing 37, such as a Sentricon Baitube. The casing 37 provides substantial isolation from the ambient environment and only termite feeding through the casing 37 ensures circuit breakage. Optionally, the casing can be covered with a lid 36.

The casing 37 material must be termite edible but need not be dimensionally stable itself. Furthermore, because the circuits are usually not placed on the casing material, the circuits need not adhere to the casing. Instead, by substantially isolating the sensor circuit 5 from the ambient environment, the sensor is effectively rendered dimensionally stable. Thus, the substrate on which the circuit is placed also need not be dimensionally stable in this embodiment such that wood or paper or other cellulose substrates can be used. Tactile stimuli (TS) sites can be formed by small indentations or notches on the casing material to further facilitate termite tunneling through the casing. Suitable environmentally isolating materials for the casing 37 include: all of the dimensional stable (DS) materials described above for use as the substrate, as well as commercial products such as Saran®, Mylar®, Polyflex®, Nitrile®, Pilofilm®, and Poliliner®, and flexible sheets made of rubber, nylon, neoprene, polyester, polyurethane, polyvinylchloride, polypropylene, polyethylene, polystyrene, polymethylpentene, polycarbonate, and polyvinyl alcohol.

The invention is illustrated further by the following examples, which are not to be construed as limiting the invention in scope or spirit to the specific procedures described in them.

EXAMPLE 1

Comparative data between wood sensors, as described in U.S. Pat. No. 5,815,090, and polymer-based DS sensors collected from two field sites are summarized in Table 1, FIG. 3 and FIG. 4. There was no termite activity in Site I during the testing. Site II was infested with a colony of the subterranean termite, *Reticulitermes flavipes*. Wood sensors and DS sensors were tested in both sites. Both sensors were placed in plastic monitoring (or Sentricon) stations as shown in FIG. 2A and installed in the soil around the structures. The sensors were grouped into 5 zones for each site, and each zone was cable-connected to a datalogger (CR10X, Campbell Scientific, Inc., Logan Utah). A multiplexer (AM416, Campbell Scientific, Inc.) was incorporated into the datalogger to allow the datalogger to monitor multiple I/O ports relating to the various sensor zones. The datalogger was designed to check circuit integrity by applying a voltage of 2,500 mV to each zone. When a given zone circuit was continuous, the voltage registered by the datalogger was approximately 2,500 mV. when the circuit was broken, the voltage was decreased to less than 2,500 mV. The multiplexer was programmed to examine the circuit integrity every 2 hours, and the data was stored in the Static Random Access Memory (SRAM) of the datalogger. The datalogger was connected to a modem and was accessible via telephone line by a host computer (Dimension XPS D266, Dell Computer, Austin Tex.). Custom software, SiteScheduler® (ADR, Inc. Auburn Hill, Mich.), in the host computer was programmed to download the data in the datalogger every 4 days. On-site inspections of the stations were made periodically to examine the causes of the circuit breakage, or the lack of it. All systems were monitored up to 12 weeks.

Datalogger readings for Site I (without termites) are presented in FIG. 3. In zone 1, sporadic and small circuit breakage was recorded numerous times approximately 6 weeks after installation of the wood sensors. On-site inspections confirmed the absence of termites, indicating false positive responses (FIG. 3A, zone 1, FP: false positive). These small breakages were typically caused by wood expansions due to excess moisture resulting from heavy rainfall. When the wood dries and contracts, the circuits re-connect as indicated by the recovery of the voltage back to 2,500 mV. At about 10 weeks, wooden sensors with broken circuits were replaced with new wood sensors (FIG. 3A, zone 1, R: replaced), but even these new wood sensors were broken by expansion from high moisture.

In zone 2, circuits on some wood sensors were broken sporadically approximately 9 weeks after installation as is evident by the false positive response (FP), presumably from the expansion of wood. The circuits self re-connect after a few days, possibly due to the drying of the wood sensors.

Zone 3 reported a true negative result (no termites and no circuit breakage) for the first 6 weeks but then showed circuit breakage (FIG. 3A, zone 3, FP). Site inspection confirmed a false positive response due to wood expansion by high humidity.

When wooden sensors are used in Site I (no termite activity), only zones 4 and 5 correctly reported unbroken circuits and thus true negative responses (TN), i.e., a consistent 2,500 mV reading throughout the 12 wk. The wood sensors in Site I correctly reported the absence of termites (TN: true negative) 87.2% of the time, but false positive responses (FP) were recorded at a high rate of 12.8% (Table 1).

When DS sensors were employed in Site I, only small circuit breakages (ca. 2,000 mV) were recorded for a relatively short period in zone 1 (FIG. 3B, FP). In zones 2–5, all DS sensors correctly reported the true negative responses (TN: absence of termite), as indicated by the consistent reading of ca. 2,500 mV. Furthermore, the rate of false positives (FP) for zones utilizing the DS sensor was only 0.1% (Table 1).

Datalogger readings for Site II (known termite activity) are shown in FIG. 4. Similar to the results in Site I, the use of wood sensors created numerous false positive responses because of wood expansion (FIG. 4A, FP, zones 1, 3, and 4). In zone 1, on-site inspections revealed that on two occasions (FP+TP) low voltage readings were caused by both termites (TP) and moisture expansion of wood sensors (FP). Because circuit breakage was frequent, it was difficult to distinguish the false positive response from actual termite activity. Wood sensors utilized in zones 2 and 5 maintained their circuit integrity by recording correctly the absence of termites. Site II had a true negative response rate (TN) of 75.9% with zones employing wood sensors while the false positive response rate of these zones was 24.1% (Table 1).

When DS sensors were used in zone 1 of Site II, voltage readings dropped to about 500 mV approximately 8 weeks after installation (FIG. 4B, zone 1). On-site inspections confirmed the true positive response (TP) as termite activity was the sole cause for the broken circuit of the DS sensor. The broken sensor was then replaced with a new DS sensor (R), which in turn was also broken by termites within a week. In zone 2, a new DS sensor replaced a first sensor after termites broke the first DS sensor just a few days after installation (FIG. 4B, zone 2, TP). The circuit on the subsequent DS sensor was again broken and on-site inspection confirmed another true positive response (TP). Similar true positive response were also recorded for zone 5. In zones 3 and 4, true negative response were confirmed by circuit continuity and absence of termites. The accuracy of DS sensors in Site II with termite activity was 100%: an 89.2% true negative response (TN) rate and a 10.8% true positive response (TP) rate (Table 1).

In summary, DS sensors correctly reported all true positive responses (TP, FIG. 4B) and virtually all (99.9%) of the true negative responses (TN, FIG. 3B, zones 2–5, and FIG. 4B, zones 3–4), while wooden sensors showed significantly lower rates. Clearly, the use of wooden sensors in a monitoring program makes it more difficult to differentiate between false positive and true positive responses.

TABLE 1

Performance* of wood or dimensionally stable (DS) sensors in a site without termite activity (Site I) and another site with known termite activity (Site II).

| Site | Sensor type | %FP | %TN | %TP |
| --- | --- | --- | --- | --- |
| I | Wood | 12.8 | 87.2 | 0.0 |
| I | DS | 0.1 | 99.9 | 0.0 |
| II | Wood | 24.1 | 75.9 | 0.0 |
| II | DS | 0.0 | 89.2 | 10.8 |

%FT: percent false positive (circuit broke in the absence of termites),
%TN: percent true negative (circuit continuity in the absence of termites),
%TP: percent true positive (circuit broken by termites).
*Figures are means of 5 zones from each site and are based on 3-month data of bi-hourly readings of circuit voltage and on-site inspection.

The invention and manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims.

I claim as my invention:

1. A dimensionally stable sensor for monitoring termite activity, comprising:

a dimensionally stable monitoring substrate having a first side and a second side, the monitoring substrate comprising a polymeric termite edible material, the polymeric termite edible material being resistant to dimensional expansion or contraction caused by changes in ambient humidity and/or temperature; and an electrically conductive circuit material affixed to or embedded in the first side of the monitoring substrate; the electrically conductive circuit material being breakable by termite activity; the electrically conductive circuit material forming a continuous electrical bridging circuit such that when termite activity breaks the electrically conductive circuit material, the continuous electrical bridging circuit is broken; the continuous electrical bridging circuit being resistant to breakage for an extended period of time from exposure to change in ambient humidity and/or temperature fluctuation such that the dimensionally stable sensor is less susceptible to false positive responses and/or false negative responses in monitoring termite activity.

2. The dimensionally stable sensor of claim 1 wherein the polymeric termite edible material is selected from the group consisting of closed-cell polyethylene, expanded polystyrene, expanded polypropylene, expanded polyurethane, textured polyethylene, vinyl, closed-cell vinyl foam, polyol resin of polymeric diisocyanate, absorbent paper with polyethylene backing, cellular rubber, and sponge rubber.

3. The dimensionally stable sensor of claim 1 wherein the electrically conductive circuit material is aluminum foil, silver particle traces, conductive epoxy glue, or particles of conductive materials bonded together with glue, the conductive materials selected from the group consisting of polymers, gold, copper, nickel or iron.

4. The dimensionally stable sensor of claim 2 wherein the termite edible material is closed-cell polyethylene.

5. The dimensionally stable sensor of claim 4 wherein the closed-cell polyethylene sheet is mounted between a first backing and a second backing, the first side of the monitoring substrate being in contact with the first backing and the second side of the monitoring substrate being in contact with the second backing, so that the continuous electrical bridging circuit is placed between the first backing and the second backing forming a tactile stimuli.

6. The dimensionally stable sensor of claim 5 wherein the first backing and the second backing are made of wood.

7. The dimensionally stable sensor of claim 1 wherein the monitoring substrate has longitudinal edges forming a tactile stimuli and containing a plurality of notches extending from the first side of the monitoring substrate to the second side of the monitoring substrate.

8. A method for continually monitoring termite activity at a site, the method comprising the steps of:

placing at least one termite sensor at the site; the termite sensor comprising a dimensionally stable monitoring substrate having a first side and a second side, the monitoring substrate comprising a polymeric termite edible material, the polymeric termite edible material being resistant to dimensional expansion or contraction caused by changes in ambient humidity and/or temperature; an electrically conductive circuit material affixed to or embedded in the first side of the monitoring substrate; the electrically conductive circuit material being breakable by termite activity; the electrically conductive circuit material forming a continuous electrical bridging circuit such that when termite activity breaks the electrically conductive circuit material, the continuous electrical bridging circuit is broken; the continuous electrical bridging circuit being resistant to breakage for an extended period of time from exposure to changes in ambient humidity and/or temperature fluctuation such that the dimensionally stable sensor is less susceptible to false positive responses and/or false negative responses in monitoring termite activity; and connecting the sensor to a detector for detecting breakage of the continuous electrical bridging circuit due to termite feeding.

9. A dimensionally stable sensor for monitoring termite activity, comprising:

a casing comprising a polymeric termite edible material that is capable of substantially isolating the monitoring substrate from the ambient environment;

a monitoring substrate made of termite edible material, the monitoring substrate being entirely enclosed in the casing; and an electrically conductive circuit material affixed to or embedded in the monitoring substrate; the electrically conductive circuit material being breakable by termite activity; the electrically conductive circuit material forming a continuous electrical bridging circuit such that when termite activity breaks the electrically conductive circuit material, the continuous electrical bridging circuit is broken.

10. The dimensionally stable sensor of claim 9 wherein the monitoring substrate is adapted to be attached to a removable lid of the casing.

11. The dimensionally stable sensor of claim 10 wherein a bottom portion of the lid of the casing includes a means for receiving the electrically conductive circuit material.

12. The dimensionally stable sensor of claim 9 wherein the casing comprises closed-cell polyethylene, expanded polystyrene, expanded polypropylene, expanded polyurethane, textured polyethylene, vinyl, closed-cell vinyl foam, polyol resin of polymeric diisocyanate, absorbent paper with polyethylene backing, cellular rubber, and sponge rubber and flexible sheets made of rubber, nylon, neoprene, polyester, polyurethane, polyvinylchloride, polypropylene, polyethylene, polystyrene, polymethylpentene, polycarbonate, and polyvinyl alcohol.

13. A method for continually monitoring termite activity at a site, the method comprising the steps of:

placing at least one termite sensor at the site; the sensor comprising a casing comprising a polymeric termite edible material, the polymeric termite edible material being capable of substantially isolating the monitoring substrate from the ambient environment; a monitoring substrate made of termite edible material, the monitoring substrate entirely enclosed in the casing; an electrically conductive circuit material affixed to or embedded in the monitoring substrate; the electrically conductive circuit material being breakable by termite activity; the electrically conductive circuit material forming a continuous electrical bridging circuit such that when termite activity breaks the electrically conductive circuit material, the continuous electrical bridging circuit is broken; and connecting the sensor to a detector for detecting breakage of the continuous electrical bridging circuit due to termite feeding.

* * * * *